United States Patent [19]

Hestermann et al.

[11] 4,150,058

[45] Apr. 17, 1979

[54] PRODUCTION OF ALKYL PHOSPHINES

[75] Inventors: Klaus Hestermann, Erfstadt Bliesheim; Gero Heymer, Erftstadt, both of Fed. Rep. of Germany

[73] Assignee: Hoechst Aktiengesellschaft, Frankfurt am Main, Fed. Rep. of Germany

[21] Appl. No.: 904,027

[22] Filed: May 8, 1978

[30] Foreign Application Priority Data

May 12, 1977 [DE] Fed. Rep. of Germany ....... 2721425

[51] Int. Cl.² .................................................. C07F 9/50
[52] U.S. Cl. ........................................... 260/606.5 P
[58] Field of Search ...................... 260/606.5 P, 583 E

[56] References Cited

U.S. PATENT DOCUMENTS

| | | | |
|---|---|---|---|
| 2,731,458 | 1/1956 | Garwood et al. | 260/606.5 P |
| 3,079,311 | 2/1963 | Hettinger | 260/606.5 P X |
| 3,099,690 | 7/1963 | Rayhut | 260/606.5 P |
| 3,760,001 | 9/1973 | Staendeke | 260/606.5 P |
| 3,855,311 | 12/1974 | Staendeke | 260/606.5 P |
| 4,052,463 | 10/1977 | Uhin et al. | 260/606.5 P |

OTHER PUBLICATIONS

Chemical Abstracts, 67, 108715j (1967).

*Primary Examiner*—Helen M. S. Sneed
*Attorney, Agent, or Firm*—Connolly and Hutz

[57] ABSTRACT

Alkyl phosphines are made. To this end, phosphorus in vapor form is reacted with steam and an alkyl amine at elevated temperature in contact with a carbon catalyst placed in a reactor, the reactants being used individually or in admixture with one another.

11 Claims, No Drawings

PRODUCTION OF ALKYL PHOSPHINES

This invention relates to a process for making alkyl phosphines of the general formula $R_nPH_{3-n}$ (I), in which R stands for different or identical alkyl groups having from 1 to 3 carbon atoms, preferably 1 carbon atom, and n stands for a whole number of 1 to 3.

Various processes for making alkyl phosphines have been described in the literature, which are all based on the alkylation of yellow phosphorus with an alkyl iodide or alkanol (Auger, V. C. R. Acad. Sci., Paris 139, 639, 671 (1904); Kosolapoff, G. M., Organophosphorus Compounds, Wiley (1950)). These processes are not, however, satisfactory inasmuch as the resulting phosphines are obtained in poor yields only and in addition to this are seriously contaminated by a series of phosphine derivatives.

In German Patent Specification "Offenlegungsschrift" No. 2,407,461, it has been suggested that $PH_3$ should be converted with an alkyl halide by heterogeneous catalysis to an alkyl phosphine. Under the conditions used in this process, quaternary phosphonium halides are obtained as additional products which precipitate on the catalyst so that it is necessary for the latter to be frequently reactivated by extraction of the phosphonium salts.

It is also known that the reaction of elemental phosporus with an alkyl halide at 280° to 420° C. in contact with active carbon produces a mixture consisting substantially of mono- and dialkylhalogeno-phosphines, which is obtained together with monor proportions of trialkyl phosphonium halides which are capable of being reacted with an alkali metal hydroxide solution to give trialkyl phosphines (cf. German Pat. Specification No. 2,116,355 and German Pat. Specification "Offenlegungsschrift" No. 2,116,439).

A disadvantage which is encountered with the process just described resides in the fact that the trialkyl phosphines are obtainable in poor yields only.

It is therefore an object of this invention to provide a single step process permitting short chain alkyl phosphines, especially methyl phosphines, to be produced in high yields from readily accessible yellow phosphorus.

This object has unexpectedly been achieved by our present process which comprises: reacting phosphorus in vapor form with steam and an alkyl amine of the general formula $R_nNH_{3-n}$ (II), in which R and n have the meanings given above, at elevated temperature in contact with a carbon catalyst placed in a reactor, the reactants being used individually or in admixture with one another.

The reaction should preferably be effected at temperatures of 280° to 350° C. The proportions of starting reactants may be varied within wide limits. It is more particularly possible to use phosphorus, steam and alkyl amine in proportions corresponding to a molar ratio of $P_4:H_2O:$alkyl amine of 1:1:1 up to 1:30:30. It is also advantageous to pass the starting reactants through the reactor at a velocity necessary to ensure a contact time with the catalyst of 1 to 200 seconds, preferably 5 to 100 seconds. A further advantageous feature provides for the starting reactants to be mixed in gas phase, for the resulting mixture to be first heated to reaction temperature and to be then contacted with the catalyst. Active carbon, especially active carbon having a BET-surface area of more than 10 m²/g, should preferably be employed as the catalyst. In order to produce predominantly primary phosphines, it is good practice to react the phosphorus with a slight stoichiometric excess of alkyl amine in contact with the catalyst over a short period of time, namely 5 to 50 seconds. Inversely, in order to produce predominantly tertiary phosphines, it is good practice to react the phosphorus with a large stoichiometric excess of the alkyl amine in contact with the catalyst over a long period of time, namely more than 50 up to about 100 seconds. The useful alkyl amines comprise more especially primary, secondary and tertiary methyl amines.

The reaction of phosphorus with water and simultaneously with an alkyl amine has not yet been described in the literature of which we are aware.

As already mentioned above, it is good practice to use 1 to 30 moles of $H_2O$ and 1 to 30 moles of alkyl amine per mol of $P_4$. In those cases in which the goal is to convert the phosphorus as completely as possible, e.g. in accordance with the following equations:

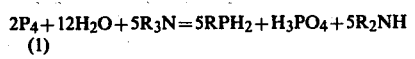

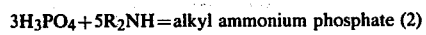

it is naturally advantageous to use an excess of $H_2$ and alkyl amine.

The reaction should preferably be effected at atmospheric pressure or under the slight overpressure which is established upon the reactants being passed through the reactor.

The reaction products coming from the reactor can be worked up by conventional methods. More specifically, they can be separated from each other by distillation; or reaction gases containing products of different basicity can be scrubbed with an acid and these products separated via the resulting phosphonium salts. Unreacted starting materials can be recycled.

The alkyl ammonium phosphates which are formed by the reaction in accordance with equation (2) deposit on the catalyst, from which they can be removed by extraction with boiling water or dilute phosphoric acid. The catalyst can then be used again. The resulting phosphate solutions are admixed with sodium hydroxide solution so as to liberate the amines, which can be recycled.

The process of this invention which is naturally not limited to the specific procedures described herein permits the production of commercial quantities of alkyl phosphines from readily accesible alkyl amines and more especially from commercially available yellow phosphorus.

The alkyl phosphines made in accordance with this invention are interesting starting materials for making flameretardant agents, pharmaceutical preparations and the like.

EXAMPLE 1

Methyl phosphines of the formulae $CH_3PH_2$; $(CH_3)_2PH$ and $(CH_3)_3P$ were made. To this end, a mixture of 0.25 mol/h of $P_4$, 3 mols/h of $H_2O$ and 1 mol/h of $(CH_3)_3N$ was heated to 290° C. in a preheater and then contacted over a period of 83 seconds at 300° C. and at atmospheric pressure with an active carbon catalyst (particle size=0.5 to 2.0 mm), which was placed in a reactor.

The reaction products coming from the reactor had different boiling points and a different basicity. They were separated from each other in known manner and the methyl phosphines were recovered in pure form. Unreacted starting material was recycled.

A total quantity of 186 g of phosphorus was used. This gave
- 85 g of $CH_3PH_2$,
- 64 g of $(CH_3)_2PH$ and
- 11 g of $(CH_3)_3P$ corresponding to a $P_4$-yield of 80%, based on equation (1).

The pure methyl phosphines had the following boiling points under 760 mm Hg:
- $CH_3PH_2$: $-15°$ C.
- $(CH_3)_2PH$: $10°-21°$ C.
- $(CH_3)_3P$: $38°-40°$ C.

The phosphines were identified in the form of their phosphonium chlorides by NMR-spectroscopy (H- and P-resonances). The spectra were taken at 90 megahertz in a strong hydrochloric acid solution. The data indicated are rounded inasmuch as they slightly depend on the HCL-concentration.

| H-resonance | | | | | P-resonance (based on $H_3PO_4$ of 85% strength) | | |
|---|---|---|---|---|---|---|---|
| $[CH_3PH_3]Cl$ | $\delta CH_3$ | 2.1 | $\delta CH_3$-P | 71 Hz | | | |
| | $\delta PH$ | 7.5 | $\delta$P-H | 555 Hz | $\delta$PH-$CH_3$ | 5 Hz | $\delta P+ 62$ |
| $[(CH_3)_2PH_2]Cl$ | $\delta CH_3$ | 2.0 | $\delta CH_3$-P | 16 Hz | | | |
| | $\delta PH$ | 6.5 | $\delta$P-H | 528 Hz | | | $\delta P+ 31$ |
| $[(CH_3)_3PH]Cl$ | $\delta CH_3$ | 1.95 | $\delta CH_3$-P | 15 Hz | $\delta CH_3$-PH | 5.5Hz | |
| | $\delta PH$ | 6.4 | $\delta$P-H | 507 Hz | | | $\delta P- 3$ |

EXAMPLE 2

$CH_3PH_2$ was made as the principal product under the conditions described in Example 1, save that the reaction temperature was 285° C. and the contact time was 35 seconds.

A total quantity of 179 g of phosphorus was used. This gave
- 84 g of $CH_3PH_2$
- 23 g of $(CH_3)_2PH$
- 3.2 g of $(CH_3)_3P$ corresponding to a $P_4$-yield of 60%, based on equation (1).

We claim:

1. A process for making alkyl phosphines of the general formula $R_nPH_{3-n}$ (I), in which R is identical or different alkyl groups having 1 to 3 carbon atoms, especially 1 carbon atom, and n is a whole number of 1 to 3, which comprises: reacting phosphorus in vapor form with steam and an alkyl amine of the general formula $R_nNH_{3-n}$ (II), in which R and n have the meanings given above, at elevated temperature in contact with a carbon catalyst placed in a reactor, the reactants being used individually or in admixture with one another.

2. The process as claimed in claim 1, wherein the reaction is effected at temperatures of 280° to 350° C.

3. The process as claimed in claim 1, wherein phosphorus, steam and alkyl amine are used in quantities corresponding to a molar ratio of $P_4$:$H_2O$:alkyl amine of 1:1:1 to 1:30:30.

4. The process as claimed in claim 1, wherein the reactants are passed through the reactor at a velocity necessary to ensure a contact time with the catalyst of 1 to 200 seconds.

5. The process claimed in claim 4, wherein the reactants are passed through the reactor at a velocity necessary to ensure a contact time with the catalyst of 5 to 100 seconds.

6. The process as claimed in claim 1, wherein the reactants are mixed in gas phase, the resulting mixture is heated to reaction temperature and then contacted with the catalyst.

7. The process as claimed in claim 1, wherein active carbon is used as the catalyst.

8. The process as claimed in claim 7, wherein the active carbon has a BET-surface area of more than 10 $m^2/g$.

9. The process as claimed in claim 1, wherein the phosphorus is reacted with a slight stoichiometric excess of alkyl amine and contacted with the catalyst over a period of about 5 to 50 seconds, with the resultant formation predominantly of primary phosphines.

10. The process as claimed in claim 1, wherein the phosphorus is reacted with a large stoichiometric excess of alkyl amine and contacted with the catalyst over a period of more than 50 up to about 100 seconds, with the resultant formation predominantly of tertiary phosphines.

11. The process as claimed in claim 1, wherein a primary, secondary or tertiary methyl amine is used as the alkyl amine.

* * * * *